US006908963B2

(12) United States Patent
Roberts et al.

(10) Patent No.: US 6,908,963 B2
(45) Date of Patent: Jun. 21, 2005

(54) THIOESTER POLYMER DERIVATIVES AND METHOD OF MODIFYING THE N-TERMINUS OF A POLYPEPTIDE THEREWITH

(75) Inventors: Michael J. Roberts, Madison, AL (US); Zhihao Fang, Madison, AL (US)

(73) Assignee: Nektar Therapeutics AL, Corporation, Huntsville, AL (US)

(*) Notice: Subject to any disclaimer, the term of this patent is extended or adjusted under 35 U.S.C. 154(b) by 544 days.

(21) Appl. No.: 09/973,318

(22) Filed: Oct. 9, 2001

(65) Prior Publication Data

US 2003/0105224 A1 Jun. 5, 2003

(51) Int. Cl.[7] .............................................. C08G 63/50
(52) U.S. Cl. ...................... 525/54.1; 525/54.2; 525/398; 525/399; 525/400; 525/437; 525/525; 525/539; 525/540
(58) Field of Search ............................... 525/54.1, 54.2, 525/398, 399, 400, 437, 535, 539, 540

(56) References Cited

U.S. PATENT DOCUMENTS

| | | | |
|---|---|---|---|
| 4,670,417 A | 6/1987 | Iwasaki et al. | |
| 4,904,584 A | 2/1990 | Shaw | |
| 5,206,344 A | 4/1993 | Katre et al. | |
| 5,252,714 A | 10/1993 | Harris et al. | |
| 5,766,897 A | 6/1998 | Braxton | |
| 5,824,784 A | 10/1998 | Kinstler et al. | |
| 5,932,462 A | 8/1999 | Harris et al. | |
| 5,985,265 A | 11/1999 | Kinstler et al. | |
| 6,057,292 A | 5/2000 | Cunningham et al. | |
| 6,184,344 B1 | 2/2001 | Kent et al. | |

FOREIGN PATENT DOCUMENTS

| | | |
|---|---|---|
| WO | WO 96/41813 | 12/1996 |
| WO | WO 98/35026 | 8/1998 |
| WO | WO 99/03887 | 1/1999 |
| WO | WO 99/24472 | 5/1999 |
| WO | WO 99/45026 | 9/1999 |
| WO | WO 99/67291 | 12/1999 |

OTHER PUBLICATIONS

Ayers, et al., "Introduction of Unnatural Amino Acids into Proteins Using Expressed Protein Ligation", *Biopolymers (Peptide Science)*, 1999, pp. 343–354, vol. 51.

Clippingdale, et al., "Peptide Thioester Preparation by Fmoc Solid Phase Peptide Synthesis for Use in Native Chemical Ligation", *J. Peptide Sci.*, 2000, pp. 225–234, vol. 6, European Peptide Society and John Wiley & Sons, Ltd.

Dawson, et al., "Synthesis of Proteins by Native Chemical Ligation", *Science,* 1994, pp. 776–779, vol. 266.

Hackeng, et al., "Protein Synthesis by Native Chemical Ligation: Expanded Scope by Using Straightforward Methodology", *Proc. Natl. Acad. Sci. USA,* 1999, pp. 10068–10073, vol. 96.

Hansen, et al., "Attachment of Antibodies to Sterically Stabilized Liposomes: Evaluation, Comparison and Optimization of Coupling Procedures", *Biochimica et Biophysica Acta 1239,* 1995, pp. 133–144.

Hershfield et al., "Use of Site–Directed Mutagenesis to Enhance the Epitope–Shielding Effect of Covalent Modification of Proteins with Polyethylene Glycol", *Proc. Natl. Acad. Sci. USA,* 1991, pp. 7185–7189, vol. 88.

Tam, et al., "Peptide Synthesis Using Unprotected Peptides Through Orthogonal Coupling Methods", *Proc. Natl. Acad. Sci. USA,* 1995, pp. 12485–12489, vol. 92.

Tam, et al., "Orthogonal Ligation Strategies for Peptide and Protein", *Biopolymers (Peptide Science)*, 1999, pp. 311–332, vol. 51, John Wiley & Sons, Inc.

Zalipsky et al., "Facile Synthesis of α–Hydroxy–ω–Carboxymethylpolyetheylene Oxide", *Journal of Bioactive and Compatible Polymers,* 1990, pp. 227–231, vol. 5.

Zalipsky, "Synthesis of an End–Group Functionalized Polyethylene Glycol–Lipid Conjugate for Preparation of Polymer–Grafted Liposomes", *Bioconjugate Chem.,* 1993, pp. 296–299, vol. 4.

Zalipsky et al., "Hydrazide Derivatives of Poly(ethylene glycol) and Their Bioconjugates", *American Chemical Society,* 1997, pp. 318–340.

*Primary Examiner*—James J. Seidleck
*Assistant Examiner*—Irina S. Zemel
(74) *Attorney, Agent, or Firm*—Alston & Bird LLP

(57) ABSTRACT

The invention provides reagents and methods for conjugating polymers specifically to the α-amine of polypeptides in high yield. The invention provides monofunctional, bifunctional, and multifunctional PEGs and related polymers having a thioester moiety capable of specifically conjugating to the α-amine of a polypeptide having a cysteine or histidine at the N-terminus. The invention provides active thioester derivatives of PEG that have suitable reactivity with an N-terminal cysteine or histidine residue of a polypeptide to produce an amide bond between the PEG and polypeptide. Use of these active esters to prepare PEG-proteins and PEG-peptides is described.

32 Claims, No Drawings

THIOESTER POLYMER DERIVATIVES AND METHOD OF MODIFYING THE N-TERMINUS OF A POLYPEPTIDE THEREWITH

FIELD OF THE INVENTION

The invention relates to polymer derivatives useful for producing polymer-modified polypeptides at their N-terminus.

BACKGROUND OF THE INVENTION

Covalent attachment of the hydrophilic polymer poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

The above polymer, alpha-,omega-dihydroxylpoly(ethylene glycol), can be represented in brief form as HO-PEG-OH where it is understood that the -PEG- symbol represents the following structural unit:

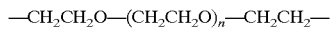

where n typically ranges from about 2 to about 4000.

PEG is commonly used as methoxy-PEG-OH, or MPEG in brief, in which one terminus is the relatively inert methoxy group, while the other terminus is a hydroxyl group that is subject to ready chemical modification. The structure of MPEG is given below.

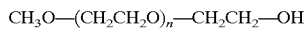

Random or block copolymers of ethylene oxide and propylene oxide, shown below, are closely related to PEG in their chemistry, and they can be substituted for PEG in many of its applications.

wherein each R is independently H or $CH_3$.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331–336 (1995).

To couple PEG to a molecule, such as a protein, it is often necessary to "activate" the PEG by preparing a derivative of the PEG having a functional group at a terminus thereof. The functional group is chosen based on the type of available reactive group on the molecule that will be coupled to the PEG. For example, the functional group could be chosen to react with an amino group on a protein in order to form a PEG-protein conjugate.

The use of polypeptides, including proteins, for therapeutic applications has expanded in recent years mainly due to improved methods for recombinant expression of human polypeptides from various expression systems and the ability to deliver these polypeptides in vivo with improved properties. Many of the drawbacks associated with polypeptide therapeutics, including short circulating half-life, immunogenicity and proteolytic degradation, can and have been improved by methods such as gene therapy, epitope mutations by directed or shuffling mutagenesis, shielding of the epitope regions by natural or synthetic polymers, fusion proteins, and incorporation of the polypeptide into drug delivery vehicles for protection and slow release.

Polymer modification of proteins, such as covalent attachment of poly(ethylene glycol), has gained popularity as a method to improve the pharmacological and biological properties of therapeutically useful proteins. For example, poly(ethylene glycol) conjugated proteins are known to have significantly enhanced plasma half-life, reduced antigenicity and immunogenicity, increased solubility and decreased proteolytic degradation. Factors that affect the foregoing properties are numerous and include the number of poly(ethylene glycol) chains attached to the protein, the molecular weight and structure of poly(ethylene glycol) chains attached to the protein, the chemistries used to attach the poly(ethylene glycol) to the protein, and the location of the poly(ethylene glycol) sites on the protein.

A variety of methods have been developed to non-specifically attach poly(ethylene glycol) to proteins. Most commonly, electrophilically-activated poly(ethylene glycol) is reacted with nucleophilic side chains found on proteins. Attaching an activated poly(ethylene glycol) to the α-amine and ε-amine groups found on lysine residues and at the N-terminus result in conjugates consisting of a mixture of products as disclosed in U.S. Pat. No. 6,057,292. For example, the conjugate may consist of a population of conjugated proteins having varying numbers of poly(ethylene glycol) molecules attached per protein molecule ("PEGmers"), ranging from zero to the number of α- and ε-amine groups in the protein. For a protein molecule that has been singly modified, the poly(ethylene glycol) moiety may be attached at any one of a number of different amine sites. This type of non-specific PEGylation can result in partial or complete loss of the therapeutic utility of the conjugated protein.

Several methods for site-directed or selective attachment of PEG have been described. For example, a site-directed approach for conjugating poly(ethylene glycol) to the N-terminal α-amine of a protein is disclosed in WO 99/45026 and U.S. Pat. Nos. 5,824,784 and 5,985,265. WO 99/03887 and U.S. Pat. Nos. 5,206,344 and 5,766,897 relate to the site-directed PEGylation of cysteine residues that have been engineered into the amino acid sequence of proteins. While these methods offer some advantages over non-specific attachment, there is a continuing need for improved methods and reagents for providing site-specific polymer conjugated proteins.

SUMMARY OF THE INVENTION

This invention provides reagents and methods for conjugating polymers specifically to the α-amine of polypeptides in high yield. The invention provides monofunctional, bifunctional, and multifunctional PEGs and related polymers having a thioester moiety capable of specifically conjugating to the α-amine of a polypeptide having a cysteine or histidine at the N-terminus. Thus, the invention provides active thioester derivatives of PEG that have suitable reactivity with an N-terminal cysteine or histidine residue of a polypeptide to produce an amide bond between the PEG and polypeptide. Use of these active esters to prepare PEG-proteins and PEG-peptides is described.

The invention provides a thioester polymer derivative comprising a water soluble and non-peptidic polymer backbone having at least one terminus bonded to the structure:

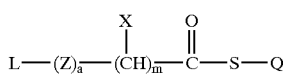

wherein,

L is the point of bonding to the polymer backbone,

Z is selected from the group consisting of —O—, —S—, —NHCO—, —CONH—, —O$_2$C—, —NHCO$_2$—, and —O$_2$CNH—, m is from 0 to about 12, preferably 1 to about 4, each X is independently selected from H and alkyl, a is 0 or 1, and Q is a leaving group.

The polymer derivative may be monofunctional, such as a derivative derived from mPEG, bifunctional, or multifunctional. The polymer backbone is preferably poly(ethylene glycol), poly(propylene glycol), or copolymers of ethylene glycol and propylene glycol. Examples of other suitable polymer backbones include other poly(alkylene glycol), poly(oxyethylated polyol), poly(olefinic alcohol), poly(vinylpyrrolidone), poly(α-hydroxy acid), poly(vinyl alcohol), polyphosphazene, polyoxazoline, poly(N-acryloylmorpholine), polyacrylate, polyacrylamides, polysaccharides, and copolymers, terpolymers, and mixtures thereof.

Examples of suitable leaving groups for use as Q include hydrogen, alkyl, substituted alkyl, aryl, substituted aryl, phenol, nitrophenol, benzoic acid, pyridine, pyridinecarboxylic acid and nitropyridine.

The invention also includes polymer conjugates of a polypeptide having a cysteine or histidine molecule at the N-terminus, the polymer conjugate comprising a water soluble and non-peptidic polymer backbone having at least one terminus bonded to the structure:

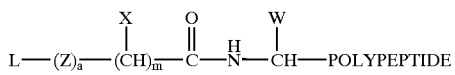

wherein

L, Z, m, X and a are as defined above,

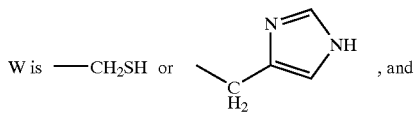

POLYPEPTIDE is the residue of the polypeptide molecule.

Examples of polypeptides that can be conjugated to the thioester polymer derivatives of the invention include, but are not limited to, protein ligands, enzymes, cytokines, hematopoietins, growth factors, hormones, antigens, antibodies, antibody fragments, receptors, and protein fragments.

A method of conjugating a polymer derivative to a polypeptide having a cysteine or histidine molecule at the N-terminus is also provided. The method comprises providing both a polypeptide having a cysteine or histidine molecule at the N-terminus and a thioester polymer derivative as described above. The polypeptide is reacted with the thioester polymer derivative to form a conjugate having an amide linkage between the residue of the N-terminal histidine or cysteine molecule and the polymer derivative. The thioester polymer derivative selectively attaches to the polypeptide at the N-terminal amine group of the histidine or cysteine molecule without reacting with free amine groups at other positions within the polypeptide.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

The term "conjugate" is intended to refer to the covalent attachment of a molecule, such as a biologically active molecule, to a polymer molecule, preferably poly(ethylene glycol). Covalent attachment means either direct coupling of the polymer to the molecule or coupling through a linker or spacer moiety.

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous medium in a matter of minutes, whereas certain esters, such as methyl or ethyl esters, require a strong catalyst in order to react with a nucleophilic group. Due to its relatively inert nature, an alkoxy group is not considered a functional group herein.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include carbonate linkages; imine linkages resulted from reaction of an amine and an aldehyde (see, e.g., Ouchi et al., Polymer Preprints, 38(1):582–3 (1997), which is incorporated herein by reference.); phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, e.g., at an end of a polymer such as PEG, and a carboxyl group of a peptide; and oligonucleotide linkages formed by a phosphoramidite group, e.g., at the end of a polymer, and a 5' hydroxyl group of an oligonucleotide.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, antiviral agents, anti-inflammatory agents, anti-tumor agents, cardiovascular agents, anti-anxiety agents, hormones, growth factors, steroidal agents, and the like.

The terms "alkyl," "alkene," and "alkoxy" include straight chain and branched alkyl, alkene, and alkoxy, respectively. The term "lower alkyl" refers to C1–C6 alkyl. The term "alkoxy" refers to oxygen substituted alkyl, for example, of the formulas —OR or —ROR$^1$, wherein R and R$^1$ are each independently selected alkyl. The terms "substituted alkyl" and "substituted alkene" refer to alkyl and alkene, respectively, substituted with one or more non-interfering substituents, such as but not limited to, C3–C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Non-interfering substituents" are those groups that yield stable compounds. Suitable non-interfering substituents or radicals include, but are not limited to, halo, $C_1$–$C_{10}$ alkyl, $C_2$–$C_{10}$ alkenyl, $C_2$–$C_{10}$ alkynyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, substituted phenyl, toluoyl, xylenyl, biphenyl, $C_2$–$C_{12}$ alkoxyalkyl, $C_7$–$C_{12}$ alkoxyaryl, $C_7$–$C_{12}$ aryloxyalkyl, $C_6$–$C_{12}$ oxyaryl, $C_1$–$C_6$ alkylsulfinyl, $C_1$–$C_{10}$ alkylsulfonyl, —(CH$_2$)$_m$—O—(C$_1$-C$_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C$_1$-C$_{10}$ alkyl), —C(O)—, —(C$_1$-C$_{10}$ alkyl), C$_2$-C$_{10}$ thioalkyl, —C(O)O-(C$_1$-C$_{10}$ alkyl), —OH, —SO$_2$, =S, —COOH, —NR$_2$, carbonyl, —C(O)—(C$_1$-C$_{10}$ alkyl)—CF$_3$, —C(O)—CF$_3$, —C(O)NR$_2$, —(C$_1$-C$_{10}$ alkyl)-S—(C$_6$-C$_{12}$ aryl), —C(O)—(C$_6$-C$_{12}$ aryl), —(CH$_2$)$_m$—O—(CH$_2$)$_m$—O—(C$_1$-C$_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

"Polypeptide" refers to any molecule comprising a series of amino acids linked through amide linkages along the alpha carbon backbone. Modifications of the peptide side chains may be present, along with glycosylations, hydroxylations, and the like. Additionally, other non-peptidic molecules, including lipids and small drug molecules, may be attached to the polypeptide.

Amino acids are listed by either the three letter or single letter abbreviations: Glycine (Gly, G), Alanine (Ala, A), Valine (Val, V), Leucine (Leu, L), Isoleucine (Ile, I), Methionine (Met, M), Proline (Pro, P), Phenylalanine (Phe, F), Tryptophan (Trp, W), Serine (Ser, S), Threonine (Thr, T), Asparagine (Asn, N), Glutamine (Gln, Q), Tyrosine, (Tyr, Y), Cysteine (Cys, C), Lysine (Lys, K), Arginine (Arg, R), Histidine (His, H), Aspartic Acid (Asp, D), and Glutamic acid (Glu, E). The present invention provides methods and reagents for conjugating poly(ethylene glycol) and other polymers to polypeptides having a specific distribution pattern with regard to the number and site of poly(ethylene glycol) attachment. The method of PEGylation results in conjugates with little or no reduction in bioactivity while preserving the beneficial properties of PEGylated biomolecules.

The invention includes thioester polymer derivatives comprising a water soluble and non-peptidic polymer backbone having at least one terminus bonded to the structure:

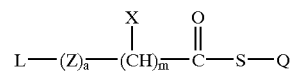

wherein,

L is the point of bonding to the polymer backbone,

Z is selected from the group consisting of —O—, —S—, —NHCO—, —CONH—, —O$_2$C—, —NHCO$_2$—, and —O$_2$CNH—, m is from 0 to about 12, preferably 1 to about 4, each X is independently selected from H and alkyl, such as C1–C6 alkyl, a is 0 or 1, and Q is a leaving group.

The polymer backbone of the water-soluble and non-peptidic polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including MPEG, bifunctional PEG, multiarmed PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—$(CH_2CH_2O)_n$—$CH_2CH_2$—, where n is from about 2 to about 4000, typically from about 20 to about 2000, is one useful polymer in the practice of the invention. PEG having a molecular weight of from about 800 Da to about 100,000 Da are particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG-OH})_m$ in which R is derived from a core moiety, such as glycerol, glycerol oligomers, or pentaerythritol, and m represents the number of arms. Another branched form, described in U.S. Pat. No. 5,932, 462, has a single terminus that is subject to ready chemical modification. This type of PEG can be represented as $(CH_3\text{O-PEG-})_pR$—X, where p equals 2 or 3, R represents a central core such as lysine or glycerol, and X represents a group such as carboxyl that is subject to ready chemical modification.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers thereof (e.g. copolymers of ethylene glycol and propylene glycol), poly (oxyethylated polyol), poly(olefinic alcohol), poly (vinylpyrrolidone), poly(α-hydroxy acid), poly(vinyl alcohol), polyphosphazene, polyoxazoline, poly(N-acryloylmorpholine), polyacrylate, polyacrylamides, polysaccharides, and copolymers, terpolymers, and mixtures thereof. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble and non-peptidic polymer backbones is by no means exhaustive and is merely illustrative, and that all polymeric materials having the qualities described above are contemplated.

The linear polymer derivatives of the invention can be structurally represented as shown below:

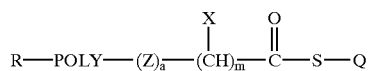

wherein POLY is a water soluble and non-peptidic polymer backbone, R is a capping group, and Z, X, m, a and Q are as defined above. In a preferred embodiment, R is methoxy, POLY is poly(ethylene glycol), a is 1, Z is O, m is 1 to about 3 and each X is H or $CH_3$.

In one embodiment, the polymer backbone is a linear poly(alkylene glycol) having the structure

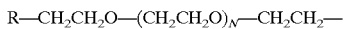

wherein R is a capping group and n is about 2 to about 4000.

Alternatively, the poly(alkylene glycol) backbone can have the structure

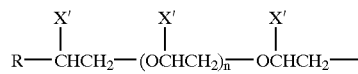

wherein R is a capping group, each X' is independently H or alkyl, such as lower alkyl, and n is about 2 to about 4000.

The R capping group can be a relatively inert capping group, such as alkoxy, alkyl, benzyl, aryl, or aryloxy, or a functional group capable of readily reacting with a functional group on a biologically active molecule. Examples of suitable functional groups include hydroxyl, protected hydroxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl ($CH_2$=CH—$CH_2$—), acrylate ($CH_2$=CH—CO—), methacrylate ($CH_2$=C($CH_3$)—CO—), acrylamide ($CH_2$=CH—CONH—$CH_2CH_2$—), active sulfone, amine ($H_2N$—$CH_2CH_2$—, ), protected amine (Y—NH—$CH_2CH_2$—, where Y is the protecting group), hydrazide, protected hydrazide, thiol (HS—$CH_2CH_2$—), protected thiol (B—S—$CH_2CH_2$—, where B is the protecting group), carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate. The functional group is typically chosen for attachment to a functional group on a biologically active agent. As would be understood, the selected capping group should be compatible with the thioester group so that reaction with the thioester group does not occur. Particularly preferred functional groups include —OH, —$NH_2$, —$CO_2H$, —CHO, N-hydroxysuccinimidyl esters, 1-benzotriazolyl esters, N-hydroxysuccinimidyl carbonates, 1-benzotriazolyl carbonates, and tresylate. The thioester polymer derivatives may be homobifunctional, meaning that the second functional group (i.e., R) is also a —$(Z)_a$—$(CXH)_m$—CO—S—Q thioester moiety, or heterobifunctional, meaning that the second functional group is a different functional group. If the PEG or other polymer derivative is heterobifunctional, it may be used to link the PEG to surfaces or other polymers, such as polysaccharides or proteins, with the other terminus attached, for example, to a drug, a liposome, another protein, or a biosensor.

As would be understood in the art, the term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide or acetate. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention.

Specific examples of terminal functional groups in the literature include N-succinimidyl carbonate (see e.g., U.S. Pat. Nos. 5,281,698, 5,468,478), amine (see, e.g., Buckmann et al. *Makromol. Chem.* 182:1379 (1981), Zaplipsky et al. *Eur. Polym. J.* 19:1177 (1983)), hydrazide (See, e.g., Andresz et al. *Makromol. Chem.* 179:301 (1978)), succinimidyl propionate and succinimidyl butanoate (see, e.g., Olson et al. in *Poly(ethylene glycol) Chemistry & Biological Applications*, pp 170–181, Harris & Zaplipsky Eds., ACS, Washington, D.C., 1997; see also U.S. Pat. No. 5,672,662), succinimidyl succinate (See, e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g., Beauchamp, et al., *Anal. Biochem.* 131:25(1983), Tondelli et al. *J. Controlled Release* 1:251(1985)), p-nitrophenyl carbonate (see, e.g., Veronese, et al., *Appl. Biochem. Biotech.*, 11:141 (1985); and Sartore et al., *Appl. Biochem. Biotech.*, 27:45 (1991)), aldehyde (see, e.g., Harris et al. *J. Polym. Sci. Chem. Ed.* 22:341 (1984), U.S. Pat. Nos. 5,824,784, Pat. No. 5,252,714), maleimide (see, e.g., Goodson et al. *Bio/Technology* 8:343 (1990), Romani et al. in *Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules*, 26:581 (1993)), vinylsulfone (see, e.g., U.S. Pat. No. 5,900,461). All of the above references are incorporated herein by reference.

The Q leaving group can be any suitable leaving group known in the art. The term "leaving group" is intended to refer to a chemical moiety that is released from a chemical reaction and that influences the rate of nucleophilic substitution proceeding by either the direct displacement or the ionization mechanism. The reactivity of leaving groups generally parallels their electron-attracting capacity. Examples include hydrogen, alkyl, substituted alkyl, aryl, substituted aryl, phenol, nitrophenol, benzoic acid, pyridine, pyridinecarboxylic acid and nitropyridine.

Some specific examples of linear polymer derivatives of the invention are shown below:

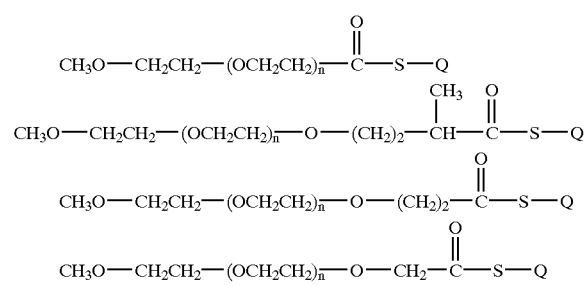

wherein Q is as defined above and n is from about 2 to about 4000, preferably about 20 to about 2000.

Multifunctional polymer derivatives are also included in the invention, such as those having the structure

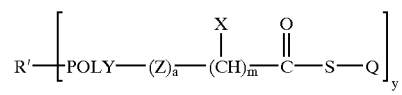

wherein each POLY is a water soluble and non-peptidic polymer backbone, R' is a non-dendritic central core molecule, y is from about 3 to about 100, and Z, X, m, a and Q are as defined above. The core moiety, R', is preferably derived from a molecule selected from the group consisting of polyols, polyamines, and molecules having a combination of alcohol and amine groups. Specific examples of central core molecules include glycerol, glycerol oligomers, pentaerythritol, sorbitol, and lysine.

The thioester polymer derivatives of the invention can be selectively reacted with the α-amine of a polypeptide having a histidine or cysteine molecule at the N-terminus to form an amide linkage between the polymer and the polypeptide. The polymer-polypeptide conjugate comprises a water soluble and non-peptidic polymer backbone having at least one terminus bonded to the structure:

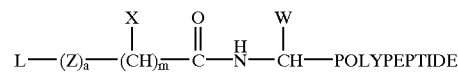

wherein
L, Z, m, X and a are defined above,

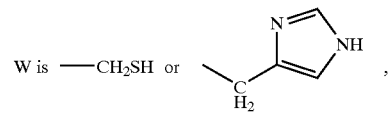

depending on whether the terminal amino acid is cysteine or histidine, and

POLYPEPTIDE is the residue of the polypeptide molecule. The polymer backbone can comprise, for example, any of the polymer structures discussed above.

The polypeptide molecule is preferably selected from the group consisting of protein ligands, enzymes, cytokines, hematopoietins, growth factors, hormones, antigens, antibodies, antibody fragments, receptors, and protein fragments. Specific examples of possible polypeptide molecules include calcitonin, parathyroid hormone, interferon alpha, interferon beta, interferon gamma, interleukins 1-21, granulocyte-colony stimulating factor, macrophage-colony stimulating factor, granulocyte-macrophage colony stimulating factor, stem cell factor, leukemia inhibitory factor, kit-ligand, flt-3 ligand, erythropoietin, thrombopoietin, tumor necrosis factor alpha, tumor necrosis factor beta, transforming growth factor, bone morphogenic proteins, osteoprotegerin, tissue plasminogen activator, platelet derived growth factor, fibroblast growth factor, keratinocyte growth factor, epidermal growth factor, human growth hormone, insulin, TRAIL, DNAse, receptors, enzymes, fusion proteins, chimeric antibodies, humanized antibodies, fully human antibodies, Fab fragments, F(ab')$_2$ fragments, Fv fragments, and scFv fragments. In one embodiment, the polypeptide is an interferon molecule.

The present invention uses a thioester derivative of a polymer such as PEG to specifically modify the α-amine of an N-terminal cysteine or histidine without modifying the remaining free functional group on the terminal amino acid. As an example, Reaction Scheme I below illustrates the reaction between a polypeptide having an N-terminal cysteine molecule and a polymer derivative of the invention. As shown, it is believed that the thioester polymer derivative initially reacts with the free thiol group of the cysteine and thereafter forms an amide linkage with the free amine group, thus leaving the thiol group available for further modification if desired. A second conjugation step can be conducted with a thiol-selective PEG derivative to produce a conjugate that has a branched structure at the N-terminus (i.e. PEG attached to both the thiol and α-amine of cysteine). The present invention is particularly useful for site-specific PEG attachment of polypeptides containing more than one free cysteine or histidine, even in the unfolded state. The current strategy can be used to assist insoluble polypeptides that are in the unfolded state to refold to their native conformation.

Thus, the invention provides a site-specific polypeptide modification method that results in a polymer-modified protein with beneficial properties including long circulating plasma half-life, reduced immunogenicity and antigenicity, reduced proteolysis, increased stability and little or no decrease in activity. The method of conjugating a polymer derivative to a polypeptide having a cysteine or histidine molecule at the N-terminus comprises providing both a polypeptide having a cysteine or histidine molecule at the N-terminus and a thioester polymer derivative as described above. The polymer derivative and the polypeptide are reacted to form a conjugate having an amide linkage between the polymer and the polypeptide.

Optionally, in the case of an N-terminal cysteine molecule, a second thiol-reactive polymer derivative may be

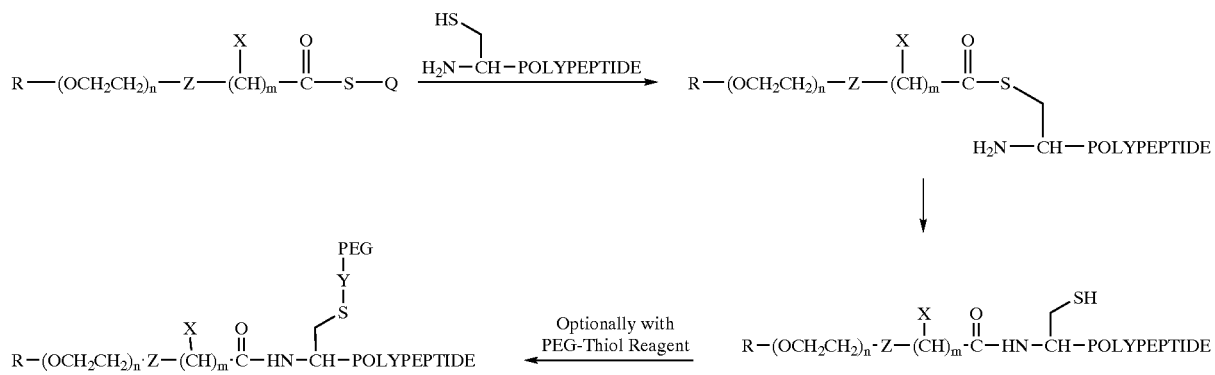

Monomethoxypoly(ethylene glycol) activated derivatives within the nominal average molecular weight range of about 200 to about 200,000 Da, and more preferably in the range of about 2000 to about 60,000 Da, are typically preferred for conjugating to proteins. Monoactivated derivatives prevent cross-linking of the protein that often occurs when bifunctional reagents are used. In the present invention, mPEG-thioester can be used to produce a single PEG molecule attached to a single protein molecule. However, utilizing a bifunctional PEG-thioester in sufficient proportions will result in a conjugate having two protein molecules attached to a single PEG molecule, even in the event the protein contains multiple free cysteine residues. Due to the manner in which the PEG derivative is believed to react (i.e. initially linking through the available thiol group and then forming the amide linkage), it is not possible for the thioester polymer derivatives of the invention to give a cross-linked protein because other free cysteine residues will not have both an available thiol group and an available amine group.

Generally, as the total molecular weight of poly(ethylene glycol) conjugated to the protein increases, antigenicity, in vitro activity, and proteolysis decrease and solubility, stability, and plasma half-life increase. Conjugates produced from the method of the invention are intended to optimize many of the beneficial properties of covalent attachment of PEG to proteins. In some instances, it may be necessary to conjugate several lower molecular weight poly(ethylene glycol) derivatives at several different sites. In other cases, it may be beneficial to attach a single large molecular weight poly(ethylene glycol) at a single specific location. In either case, it is the focus of the invention to produce a conjugate that offers a high degree of control over the conjugation site and, therefore, control of the enhanced properties.

reacted with the free thiol group in order to form a branched structure at the terminus of the polypeptide as shown in Reaction Scheme I, wherein PEG represents the second polymer backbone, although other polymer backbones could be used as described above, and Y is the linker resulting from the reaction of the thiol-reactive terminal functional group of the PEG derivative with the free thiol group on the cysteine molecule. In one embodiment, only two polymer backbones are attached to the polypeptide. Examples of thiol-reactive functional groups include vinylsulfone, maleimide, orthopyridyl disulfide and iodoacetamide. Examples of the Y linkage include:

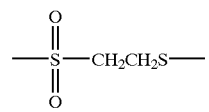

(resulting from vinylsulfone functional group)

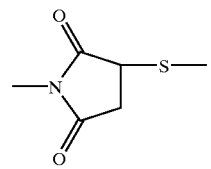

(resulting from maleimide functional group)

—S—S—

(resulting from orthopyridyl disulfide functional group)

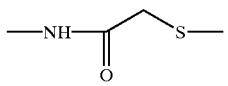

(resulting from iodoacetamide functional group)

As would be readily understood by one of ordinary skill in the art, the method of the invention could be used to couple the above-described polymer derivatives to any moiety, whether peptidic or not, having a terminal —CH(W)—NH$_2$ group, wherein W is as defined above.

The following examples are given to illustrate the invention, but should not be considered in limitation of the invention.

EXAMPLE 1

PEG(5000)-α-methoxy-ω-propionic acid, 2-pyridylthioester (PEG-PA-OPTE)

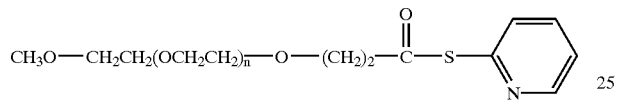

2-mercaptopyridine (40.0 mg, 0.36 mmoles), 1-hydroxybenzotriazole (4.0 mg, 0.030 mmoles), 4-(dimethylamino)pyridine (36.7 mg, 0.30 mmoles) and 1,3-dicyclohexylcarbodiimide (dissolved in 2 mL anhydrous dichloromethane, 84.0 mg, 0.41 mmoles) were added to a solution of PEG(5000)-α-methoxy-ω-propionic acid (1.5 g, 0.27 mmoles) in anhydrous acetonitrile (20 mL). The reaction solution was stirred overnight at ambient temperature under argon. The solution was then concentrated to near dryness at reduced pressure, followed by addition of anhydrous toluene (50 mL). The mixture was stirred at room temperature for thirty minutes, filtered and the filtrate was concentrated at reduced pressure to near dryness. Ethyl acetate (200 mL) was added and the mixture was warmed until the contents were completely dissolved. The solution was then cooled to room temperature while stirring. Ethyl ether (50 mL) was added and a precipitate formed. The product was filtered and rinsed with ethyl ether until the product became white. The product was then dried under high vacuum. Yield: 1.1 g. NMR (d6-DMSO): δ2.98 ppm (t, 2H, —CH$_2$—COS—), δ3.51 ppm (s, PEG backbone), δ7.46 ppm (m, ill resolved, 1H, H$_5$ (pyridyl)), δ7.64 ppm (d, 1H, H$_3$ (pyridyl)), δ7.91 ppm (t, 1H, H$_4$ (pyridyl)), δ8.60 ppm (d, 1H, H$_6$ (pyridyl)).

EXAMPLE 2

PEG(5000)-α-benzyloxy-ω-carboxymethyl, 2-pyridylthioester (PEG-CM-OPTE)

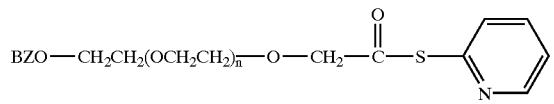

2-mercaptopyridine (40.0 mg, 0.36 mmoles), 1-hydroxybenzotriazole (5.0 mg, 0.035 mmoles), and 1,3-dicyclohexylcarbodiimide (dissolved in 2 mL anhydrous dichloromethane, 74.3 mg, 0.36 mmoles) were added to a solution of PEG(5000)-α-benzyloxy-ω-carboxymethyl (1.5g, 0.30 mmoles) in anhydrous acetonitrile (20 mL). The reaction solution was stirred overnight at ambient temperature under argon. The solution was then concentrated to near dryness at reduced pressure, followed by addition of anhydrous toluene (30 mL). The mixture was stirred at room temperature for thirty minutes, filtered and the filtrate was concentrated at reduced pressure to near dryness. Ethyl acetate (150 mL) was added and the mixture was warmed until the contents were completely dissolved. The solution was then cooled to room temperature while stirring. Ethyl ether (50 mL) was added to the solution and a precipitate formed. The product was filtered and rinsed with ethyl ether until the product became white. The product was then dried under high vacuum. Yield: 1.1 g. NMR (d6-DMSO): δ3.51 ppm (s, PEG backbone), δ4.39 ppm (s, 2H, —OCH$_2$COS—), δ4.49 ppm (s, 2H, —OCH$_2$-(benzyloxy)), δ7.33 ppm (m, ill resolved, 5H, C$_6$H$_5$ (benzyloxy)), δ7.46 ppm (m, ill resolved, 1H, H$_5$ (pyridyl)), δ7.63 ppm (d, 1H, H$_3$ (pyridyl)), δ7.91 ppm (t, 1H, H$_4$ (pyridyl)), δ8.60 ppm (d, 1H, H$_6$ (pyridyl)).

EXAMPLE 3

PEG(5000)-α-methoxy-ω-2-methyl butanoic acid, 2-pyridylthioester

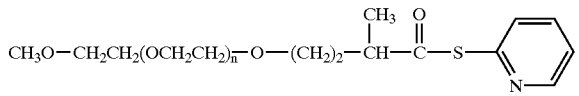

2-mercaptopyridine (44.5 mg, 0.40 mmoles), 1-hydroxybenzotriazole (4.7 mg, 0.033 mmoles), 4-(dimethylamino)pyridine (40.7 mg, 0.33 mmoles) and 1,3-dicyclohexylcarbodiimide (dissolved in 2 mL anhydrous dichloromethane, 92.8 mg, 0.45 mmoles) were added to a solution of PEG(5000)-α-methoxy-ω-2-methyl butanoic acid (1.5 g, 0.30 mmoles) in anhydrous acetonitrile (20 mL). The reaction solution was stirred overnight at ambient temperature under argon. The solution was then concentrated to near dryness at reduced pressure, followed by addition of anhydrous toluene (50 mL). The mixture was stirred at room temperature for thirty minutes, filtered and the filtrate was concentrated at reduced pressure to near dryness. Ethyl acetate (150 mL) was added and mixture was warmed until the contents completely dissolved. The solution was then cooled to room temperature while stirring. A precipitate was formed by adding 2-Propanol (50 mL), followed by addition of ethyl ether (50 mL). The product was filtered off, rinsed with 2-propanol until the product became white. The product was then dried under high vacuum. Yield: 1.2 g. NMR (d6-DMSO): δ1.19 ppm (d, 3H, —O—CH$_2$—CH$_2$—CH(CH$_3$)—COS—), δ1.66 ppm and δ1.92 ppm (mm, 2H, —O—CH$_2$—CH$_2$—CH(CH$_3$)—COS—), δ2.89 ppm (m, 1H, —O—CH$_2$—CH$_2$—CH(CH$_3$)—COS—), δ3.51 ppm (s, PEG backbone), δ7.46 ppm (m, ill resolved, 1H, H$_5$ (pyridyl)), δ7.63 ppm (d, 1H, H$_3$ (pyridyl)), 67.90 ppm (t, 1H, H$_4$ (pyridyl)), δ8.60 ppm (d, 1H, H$_6$ (pyridyl)).

EXAMPLE 4

Conjugation of PEG-CM-OPTE to Interferon

Interferon tau (0.45 mg), which has a cysteine as the N-terminal amino acid, was formulated to 0.3 mg/ml in 1M Tris, 0.7 mM TCEP (Tris[2-carboxyethylphosphine]

hydrochloride) and 3 mM mercaptopropionic acid at pH 7.75. Approximately 1.0 mg of mPEG$_{5K}$-CM-OPTE was added to the interferon solution and allowed to react at room temperature for 4 hours. The reaction mixture was dialyzed against deionized water overnight. The product was analyzed by MALDI-MS. The mass spectrum showed free PEG at 5000 Da, unconjugated interferon at 19,979 Da and a single PEG conjugate at a molecular weight of 25,065 Da.

EXAMPLE 5

Conjugation of PEG-PA-OPTE to Interferon

Interferon tau (0.45 mg) was formulated to 0.3 mg/ml in 0.33M Tris, 0.7 mM TCEP (Tris[2-carboxyethylphosphine] hydrochloride) at pH 7.75. Approximately 1.0 mg of mPEG$_{5K}$-PA-OPTE (orthopyridyl thioester of propionic acid) was added to the interferon solution and allowed to react at room temperature for 4 hours. The product was analyzed by SDS-PAGE. The gel showed two bands corresponding to unconjugated interferon (~20 kDa) and singly PEG-conjugated interferon (~29 kDa). The slower migration of the PEG-interferon conjugate is due to the larger hydrodynamic volume of the PEG chain when compared to a corresponding molecular weight protein.

EXAMPLE 6

Conjugation of PEG-CM-OPTE to a Polypeptide

The polypeptide CRASKSVSSSGYSYMHWYQQ (MW=2355 Da), was formulated to 0.67 mg/ml in 0.67M Tris, 1.3 mM TCEP (Tris[2-carboxyethylphosphine] hydrochloride) and 5.3M urea at pH 7.75. Approximately 21.0 mg of mPEG$_{5K}$-CM-OPTE was added to the polypeptide solution and allowed to react at room temperature for 4 hours. The reaction mixture was dialyzed against deionized water overnight. The product was analyzed by MALDI-MS. The mass spectrum showed a single PEG-peptide conjugate having a molecular weight of 7555 Da.

EXAMPLE 7

Conjugation of PEG-PA-OPTE to a Polypeptide

The polypeptide CRASKSVSSSGYSYMHWYQQ (MW=2355 Da), was formulated to 0.67 mg/ml in 0.67M Tris, 1.3 mM TCEP (Tris[2-carboxyethylphosphine] hydrochloride) and 5.3M urea at pH 7.75. Approximately 21.0 mg of mPEG$_{5K}$-PA-OPTE was added to the polypeptide solution and allowed to react at room temperature for 4 hours.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A thioester polymer derivative, comprising a water soluble and non-peptidic polymer backbone having at least one terminus bonded to the structure:

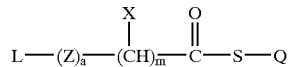

wherein,

L is the point of bonding to the polymer backbone,

Z is selected from the group consisting of —O—, —S—, —NHCO—, —CONH—, —O$_2$C—, —NHCO$_2$—, and —O$_2$CNH—, m is from 0 to about 12, each X is independently selected from H and alkyl, a is 0 or 1, and Q is a leaving group.

2. The polymer derivative of claim 1, wherein the polymer backbone is selected from the group consisting of poly (alkylene glycol), poly(oxyethylated polyol), poly(olefinic alcohol), poly(vinylpyrrolidone), poly(α-hydroxy acid), poly(vinyl alcohol), polyphosphazene, polyoxazoline, poly (N-acryloylmorpholine), polyacrylate, polyacrylamides, polysaccharides, and copolymers, terpolymers, and mixtures thereof.

3. The polymer derivative of claim 1, wherein said water soluble and non-peptidic polymer backbone is selected from the group consisting of poly(ethylene glycol), poly (propylene glycol), and copolymers of ethylene glycol and propylene glycol.

4. The polymer derivative of claim 1, wherein the polymer backbone is poly(ethylene glycol).

5. The polymer derivative of claim 4, wherein the poly (ethylene glycol) has an average molecular weight from about 800 Da to about 100,000 Da.

6. The polymer derivative of claim 1, wherein the polymer backbone has about 2 to about 300 termini.

7. The polymer derivative of claim 1, wherein the polymer backbone has the structure

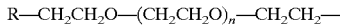

wherein R is a capping group and n is about 2 to about 4000.

8. The polymer derivative of claim 7, wherein R is selected from the group consisting of alkoxy, alkyl, benzyl, aryl, aryloxy, hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate or —(Z)$_a$—(CXH)$_m$—CO—S—Q, wherein Z, X, m, a and Q are as defined above.

9. The polymer derivative of claim 1, wherein the polymer backbone has the structure

wherein R is a capping group, each X' is independently H or alkyl, and n is about 2 to about 4000.

10. The polymer derivative of claim 9, wherein R is selected from the group consisting of alkoxy, alkyl, benzyl, aryl, aryloxy, hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate or —$(Z)_a$—$(CXH)_m$—CO—S—Q, wherein Z, X, m, a and Q are as defined above.

11. The polymer derivative of claim 1, wherein Q is selected from the group consisting of hydrogen, alkyl, substituted alkyl, aryl, substituted aryl, phenol, nitrophenol, benzoic acid, pyridine, pyridinecarboxylic acid and nitropyridine.

12. The polymer derivative of claim 1, wherein Q is pyridine.

13. The polymer derivative of claim 1, wherein a is 1 and Z is O.

14. The polymer derivative of claim 1, wherein m is 1 to about 4.

15. The polymer derivative of claim 1, having the structure:

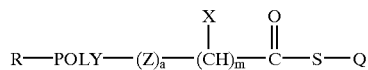

wherein POLY is a water soluble and non-peptidic polymer backbone, R is a capping group, and Z, X, m, a and Q are as defined above.

16. The polymer derivative of claim 15, wherein R is selected from the group consisting of alkoxy, alkyl, benzyl, aryl, aryloxy, hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate or —$(Z)_a$—$(CXH)_m$—CO—S—Q, wherein Z, X, m, a and Q are as defined above.

17. The polymer derivative of claim 15, wherein POLY is selected from the group consisting of poly(alkylene glycol), poly(oxyethylated polyol), poly(olefinic alcohol), poly(vinylpyrrolidone), poly(α-hydroxy acid), poly(vinyl alcohol), polyphosphazene, polyoxazoline, poly(N-acryloylmorpholine), polyacrylate, polyacrylamides, polysaccharides, and copolymers, terpolymers, and mixtures thereof.

18. The polymer derivative of claim 15, wherein POLY is selected from the group consisting of poly(ethylene glycol), poly(propylene glycol), and copolymers of ethylene glycol and propylene glycol.

19. The polymer derivative of claim 15, wherein POLY is poly(ethylene glycol).

20. The polymer derivative of claim 15, wherein Q is selected from the group consisting of hydrogen, alkyl, substituted alkyl, aryl, substituted aryl, phenol, nitrophenol, benzoic acid, pyridine, pyridinecarboxylic acid and nitropyridine.

21. The polymer derivative of claim 15, wherein Q is pyridine.

22. The polymer derivative of claim 15, wherein a is 1 and Z is 0.

23. The polymer derivative of claim 15, wherein m is 1 to about 4.

24. The polymer derivative of claim 15, wherein a and m are 0.

25. The polymer derivative of claim 1, having the structure:

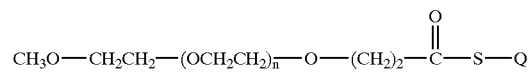

wherein Q is as defined above and n is from about 2 to about 4000.

26. The polymer derivative of claim 1, having the structure:

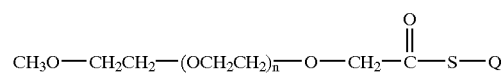

wherein Q is as defined above and n is from about 2 to about 4000.

27. The polymer derivative of claim 1, having the structure:

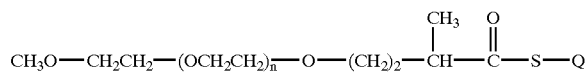

wherein Q is as defined above and n is from about 2 to about 4000.

28. The polymer derivative of claim 1, having the structure:

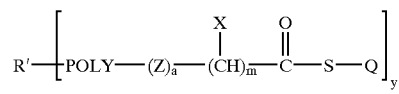

wherein each POLY is a water soluble and non-peptidic polymer backbone, R' is a non-dendritic central core molecule, y is from about 3 to about 100, and Z, X, m, a and Q are as defined above.

29. The polymer derivative of claim 28, wherein POLY is selected from the group consisting of poly(alkylene glycol), poly(oxyethylated polyol), poly(olefinic alcohol), poly(vinylpyrrolidone), poly(α-hydroxy acid), poly(vinyl alcohol), polyphosphazene, polyoxazoline, poly(N-acryloylmorpholine), polyacrylate, polyacrylamides, polysaccharides, and copolymers, terpolymers, and mixtures thereof.

30. The polymer derivative of claim 28, wherein POLY is poly(ethylene glycol).

31. The polymer derivative of claim 28, wherein R' is derived from a molecule selected from the group consisting of polyols, polyamines, and molecules having a combination of alcohol and amine groups.

32. The polymer derivative of claim 28, wherein R' is derived from a molecule selected from the group consisting of glycerol, glycerol oligomers, pentaerythritol, sorbitol, and lysine.

* * * * *